(12) United States Patent
Böttcher et al.

(10) Patent No.: US 6,462,056 B1
(45) Date of Patent: Oct. 8, 2002

(54) OXAZOLIDINES AS 5-HT$_{2A}$-ANTAGONISTS

(75) Inventors: Henning Böttcher, Darmstadt (DE);
Helmut Prücher, Heppenheim (DE);
Hartmut Greiner, Weiterstadt (DE);
Gerd Bartoszyk, Weiterstadt (DE);
Christoph Seyfried, Darmstadt (DE)

(73) Assignee: Merck Patent Gesellschaft mit beschrankter Haftung (DE)

( * ) Notice: Subject to any disclaimer, the term of this patent is extended or adjusted under 35 U.S.C. 154(b) by 0 days.

(21) Appl. No.: 09/380,202

(22) PCT Filed: Feb. 6, 1998

(86) PCT No.: PCT/EP98/00637

§ 371 (c)(1),
(2), (4) Date: Oct. 25, 1999

(87) PCT Pub. No.: WO98/38189

PCT Pub. Date: Sep. 3, 1998

(30) Foreign Application Priority Data

Feb. 26, 1997 (DE) .......................... 197 07 628

(51) Int. Cl.$^7$ ................. A61K 31/454; A61K 31/4525; C07D 413/14
(52) U.S. Cl. ...................... 514/323; 514/638; 514/657; 546/201; 558/411
(58) Field of Search ................. 514/323, 638, 514/657; 546/201; 558/411

(56) References Cited

FOREIGN PATENT DOCUMENTS

| | | |
|---|---|---|
| DE | 3723797 | 1/1989 |
| EP | 0459256 | 12/1991 |
| EP | 0635505 | 1/1995 |
| EP | 0722942 | 7/1996 |
| WO | 9200070 | 1/1992 |

OTHER PUBLICATIONS

Morrison & Boyd, Organic Chemistry, 3rd ed. 1973, pp. 286.*

* cited by examiner

*Primary Examiner*—T. A. Solola
(74) *Attorney, Agent, or Firm*—Millen, White, Zelano & Branigan, P.C.

(57) ABSTRACT

The invention relates to novel oxazolidine derivatives of the formula

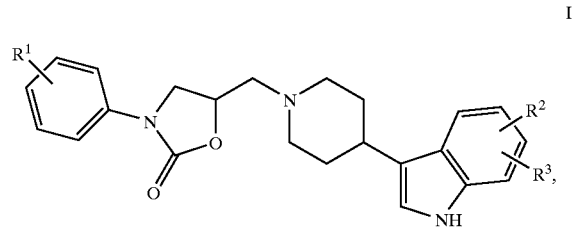

I in which $R^1$, $R^2$ and $R^3$ have the meanings stated in claim 1, their salts and processes for preparing the compounds according to the invention.

The compounds of the formula I act as 5-HT$_{2A}$ antagonists with a 5-HT reuptake-inhibiting, antidepressant or anxiolytic effect and can be used to produce pharmaceuticals.

13 Claims, No Drawings

OXAZOLIDINES AS 5-HT$_{2A}$-ANTAGONISTS

This Application is a 371 of PCT/EP98/00637 filed Feb. 6, 1998.

The invention relates to compounds of the formula I

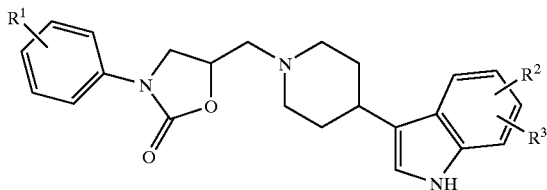

in which
- R$^1$ is H, CN, Hal or OA,
- R$^2$, R$^3$ are each, independently of one another, H, CN, Hal or OA,
- R$^2$ and R$^3$ together are also methylenedioxy,
- A is H, CF$_3$ or alkyl with 1–6 C atoms and
- Hal is F, Cl, Br, I, and the salts thereof.

5-[(2-Oxobenzimidazolin-1-yl)piperidinomethyl]-oxazolidin-2-ones with effects on the central nervous system are disclosed, for example, in EP 0 443 197. Indolepiperidines N-alkylated by indolalkyl radicals are described, for example, in EP 0 683 16. 3-Phenyl-5-[(4-R-X-piperidino)alkyl]oxazolidin-2-one derivatives in which R is phenyl and X is —O—, —S—, —SO— or —SO$_2$— and which have effects on the central nervous system are disclosed, for example, in EP 0 635 505. Indolepiperidine derivatives with a tricyclic radical and effects on the central nervous system are described, for example, in EP 0 722 942. 4-Aryl-1-(indan-, dihydrobenzofuran- or dihydrobenzothiophenemethyl)-piperidine derivatives with an effect on serotoninergic and dopaminergic transmission and with an inhibiting effect on 5-HT reuptake are described, for example, in WO 95/33721.

The invention was based on the object of finding novel compounds with valuable properties, in particular those which can be used to produce pharmaceuticals.

It has been found that, while being well tolerated, compounds of the formula I and their salts have particularly valuable pharmacological properties because they display effects on the central nervous system, in particular dopamine-antagonistic and 5-HT reuptake-inhibiting effects since they influence both serotoninergic and dopaminergic transmission. In particular, they have affinities for the 5-HT$_{1A}$ and/or 5-HT$_{2A}$ receptors.

The compounds of the formula I inhibit the binding of tritiated serotonin receptor ligands to hippocampal receptors (Cossery et al., European J. Pharmacol. 140 (1987), 143–155) and inhibit synaptosomal serotonin reuptake (Sherman et al., Life Sci. 23 (1978), 1863–1870). In particular, they bind to 5-HT$_{2A}$ and D$_2$ receptors. In addition, changes in DOPA accumulation in the striatum and 5-HTP accumulation in the raphe nuclei occur (Seyfried et al., European J. Pharmacol. 160 (1989), 31–41). The 5-HT$_{1A}$-antagonistic effect is detected in vitro for example by inhibition of the abolition caused by 8-OH-DPAT in the electrically induced contraction of the guineapig ileum (Fozard and Kilbinger, Br. J. Pharmacol. 86 (1985) 601P). The 5-HT$_{1A}$-antagonistic effect is detected ex vivo by the inhibition of 5-HTP accumulation reduced by 8-OH-DPAT (Seyfried et al., European J. Pharmacol. 160 (1989), 31–41).

Ex vivo inhibition of serotonin reuptake is detected by means of synaptosomal uptake inhibition (Wong et al., Neuropsychopharmacol. 8 (1993), 23–33) and p-chloroamphetamine antagonism (Fuller et al., J. Pharmacol. Exp. Ther. 212 (1980), 115–119). The pharmacological tests can moreover be carried out in analogy to the methods described in WO 95/33721.

The compounds of the formula I are therefore suitable both in veterinary medicine and in human medicine for treating central nervous system dysfunctions. They can be used for the prophylaxis and control of the sequelae of cerebral infarctions (apoplexia cerebri) such as stroke and cerebral ischaemias, and for the treatment of extrapyramidal motor side effects of neuroleptics, and of Parkinson's disease. However, they are particularly suitable as pharmaceutical active substances for anxiolytics, anti-depressants, antipsychotics and/or for the treatment of obsessive-compulsive disorder (OCD), anxiety states, panic attacks, depressions, psychoses, schizophrenia, delusional obsessions, Alzheimer's disease, migraine, anorexia, sleep disturbances, tardive dyskinesias, learning disorders, age-related memory impairments, eating disorders such as bulimia, substance abuse and/or sexual dysfunctions.

The compounds of the formula I and their physiologically acceptable acid addition salts can therefore be used as pharmaceutical active substances for anxiolytics, antidepressants, antipsychotics, neuroleptics and/or antihypertensives, and for beneficially influencing obsessive-compulsive disorder, eating disorders such as Bulimia, tardive dyskinesias, learning disorders and age-related memory impairments. They can furthermore be employed as intermediates for preparing other pharmaceutical active substances.

The invention thus relates to compounds of the formula I and to their physiologically acceptable acid addition salts.

The invention accordingly relates to the compounds of the formula I and to a process for preparing compounds of the formula I, characterized in that a) a compound of the formula II

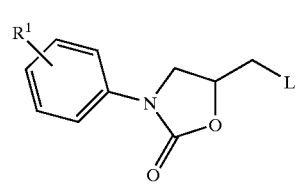

in which R$^1$ has the meaning stated in Claim 1, and L is Cl, Br, I or a free or reactively functionally modified OH group, is reacted with a compound of the formula III

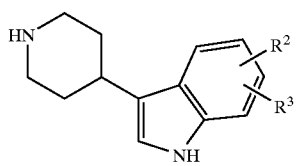

in which R$^2$ and R$^3$ have the meanings given in Claim 1, or b) a compound of the formula IV

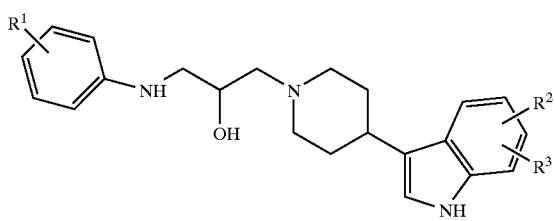

in which $R^1$, $R^2$ and $R^3$ have the meanings stated in Claim 1,
is reacted with a compound of the formula V

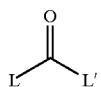

in which L and L' are each, independently of one another, Cl, Br, I or a free or reactively functionally modified OH group, or c) a compound of the formula VI

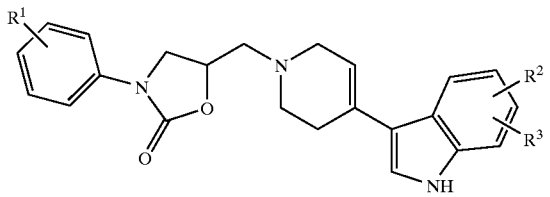

in which $R^1$, $R^2$ and $R^3$ have the meanings stated in Claim 1, is hydrogenated,
and/or in that a basic compound of the formula I is converted by treatment with an acid into one of its salts.

Hereinbefore and hereinafter, the radicals $R^1$, $R^2$, $R^3$ and L have the meanings stated for formulae I, II, III, IV and V unless expressly stated otherwise.

The invention likewise relates to pharmaceuticals of the formula I and their physiologically acceptable salts with $5\text{-}HT_{1A}$- and $5\text{-}HT_{2A}$-antagonistic and 5-HT reuptake-inhibiting effects.

The invention relates to the compounds of the formula I according to Claim 1 and to the enantiomers thereof and the salts thereof.

It applies to all radicals which occur more than once, such as, for example, A, that their meanings are independent of one another.

Alkyl has 1 to 10, preferably 1, 2, 3, 4, 5 or 6 C atoms. Alkyl is therefore in particular, for example, methyl, furthermore ethyl, propyl, isopropyl, butyl, isobutyl, sec-butyl or tert-butyl, also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-,; 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, also fluoromethyl, difluoromethyl, trifluoromethyl, 1,1,1-trichloroethyl or pentafluoro-ethyl.

A—C— is hydroxyl or alkoxy, in particular, for example, methoxy, ethoxy, propoxy or butyloxy.

The compounds of the formula I, and the starting materials for preparing them, are moreover prepared by methods known per se, as described in the literature (for example in the standard works such as Houben-Weyl, Methoden der organischen Chemie [Methods of Organic Chemistry] Georg-Thieme-Verlag, Stuttgart), specifically under reaction conditions known and suitable for the reactions mentioned. It is moreover possible to make use of variants which are known per se but which are not mentioned here in detail.

L in the compounds of the formula II, and L and L' in the compounds of the formula V, are in each case independently of one another, Cl, Br, I or a free or reactive esterified OH group.

If L is a reactive esterified OH group, this is preferably trichloromethoxy, alkoxy such as, for example, methoxy, ethoxy, propoxy or butoxy, furthermore phenoxy, alkylsulfonyloxy with 1–6 C atoms (preferably methylsulfonyloxy) or arylsulfonyloxy with 6–10 C atoms (preferably phenyl- or p-tolylsulfonyloxy, also 2-naphthalenesulfonyloxy). L in the compounds of the formula V in particular is Cl, 1-imidazolyl, ethoxy, trichloromethoxy, phenoxy or nitrophenoxy.

The starting materials can, if required, also be formed in situ so that they are not isolated from the reaction mixture but are immediately reacted further to give the compounds of the formula I. It is possible on the other hand to carry out the reaction stepwise.

The compounds of the formula I can preferably be obtained by reacting compounds of the formula II with compounds of the formula III.

The starting materials of the formulae II and III are known in some cases. If they are not known, they can be prepared by methods known per se.

Primary alcohols of the formula II can be obtained, for example, by reducing the corresponding carboxylic acids or their esters. Treatment with thionyl chloride, hydrogen bromide, phosphorus tribromide or similar halogenated compounds affords the corresponding halides of the formula II.

3-(4-Piperidyl)indoles of the formula III can be prepared, for example, by reacting 4-piperidones with indole or corresponding $R^2$- and/or $R^3$-substituted derivatives with subsequent acid treatment and hydrogenation.

The reaction of compounds of the formula II with compounds of the formula III usually takes place in an inert solvent in the presence of an acid-binding agent, preferably of an alkali metal or alkaline earth metal hydroxide, carbonate or bicarbonate or of another salt of a weak acid of the alkali metals or alkaline earth metals, preferably of potassium, sodium, calcium or caesium. Addition of an organic base such as triethylamine, dimethylaniline, pyridine or quinoline may also be beneficial. The reaction time depends on the conditions used and is between a few minutes and 14 days, and the reaction temperature is between about 0° and 150°, normally between 20° and 130°.

Examples of suitable inert solvents are hydrocarbons such as hexane, petroleum ether, benzene, toluene or xylene; chlorinated hydrocarbons such as trichloroethylene, 1,2-dichloroethane, tetrachloromethane, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methylglycol or ethylglycol), ethylene glycol dimethyl ether (diglyme); ketones such as acetone or butanone; amides such as acetamide, dimethylacetamide or dimethylformamide (DMF); nitriles such as acetonitrile;

sulfoxides such as dimethyl sulfoxide (DMSO); carbon disulfite; carboxylic acids such as formic acid or acetic acid; nitro compounds such as nitromethane or nitrobenzene; esters such as ethyl acetate or mixtures of the solvents mentioned.

Compounds of the formula I can furthermore be obtained preferably by reacting compounds of the formula IV with compounds of the formula V. Suitable and preferred compounds of the formula V are dialkyl carbonates such as dimethyl, ditrichloromethyl or diethyl carbonate, chloroformic esters such as methyl or ethyl chloroformate, N,N'-carbonyldiimidazole or phosgene.

Some of the starting materials of the formulae IV and V are known. If they are unknown, they can be prepared by methods known per se. The reaction takes place in solvents and at temperatures as described above.

Compounds of the formula VI can furthermore be converted by reduction into compounds of the formula I. This is preferably carried out by catalytic hydrogenation with, for example, palladium on active carbon and hydrogen.

Some of the starting materials of the formula VI are known. If they are unknown, they can be prepared by methods known per se. Reduction takes place in solvents and at temperatures as described above.

It is furthermore possible to convert a compound of the formula I in which $R^1$ is OH by alkylation into an ether compound of the formula I in which $R^2$ is alkoxy.

A base of the formula I can be converted with an acid into the relevant acid addition salt, for example by reacting equivalent amounts of the base and of the acid in an inert solvent such as ethanol and subsequently evaporating. Particularly suitable acids for this reaction are those which afford physiologically acceptable salts. Thus, it is possible to use inorganic acids, for example sulfuric acid, nitric acid, hydrohalic acids such as hydrochloric acid or hydrobromic acid, phosphoric acids such as ortho-phosphoric acid, sulfamic acid, also organic acids, in particular aliphatic, alicyclic, araliphatic, aromatic or heterocyclic mono- or polybasic carboxylic, sulfonic or sulfuric acid, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, lauryl sulfuric acid. Salts with physiologically unacceptable acids, for example picrates, can be used to isolate and/or purify compounds of the formula I.

Compounds of the formula I according to the invention may, because of their molecular structure, be chiral and may accordingly occur in two enantiomeric forms. They may therefore exist in racemic or in optically active form.

Since the racemates and stereoisomers of the compounds according to the invention may differ in pharmaceutical activity, it may be desirable to use the enantiomers. It is possible in these cases for the final product or else the intermediates to be fractionated into enantiomeric compounds by chemical or physical procedures known to the skilled person, or to be employed as such in the synthesis.

In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline) or the various optically active camphorsulfonic acids. It is also advantageous to separate the enantiomers by chromatography using an optically active resolving agent (for example dinitrobenzoylphenylglycine, cellulose triacetate or other derivatives of carbohydrates or chirally derivatized methacrylate polymers immobilized on silica gel). Suitable mobile phases for this purpose are aqueous or alcoholic solvent mixtures such as, for example, hexane/isopropanol/acetonitrile, for example in the ratio 82:15:3.

Salts with physiologically unacceptable acids, for example picrates, can be used to isolate and/or purify compounds of the formula I.

The invention furthermore relates to the use of compounds of the formula I and/or their physiologically acceptable salts for producing pharmaceutical compositions, in particular by non-chemical means. For this purpose they can be converted together with at least one solid or liquid and/or semiliquid excipient or ancillary substances and, where appropriate, in combination with one or more other active substances into a suitable dosage form.

The invention furthermore relates to pharmaceutical compositions comprising at least one compound of the formula I and/or one of its physiologically acceptable salts.

The compositions can be used as pharmaceuticals in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatin, carbohydrates such as lactose or starch, magnesium stearate, talc, petrolatum. Used for oral administration are, in particular, tablets, pills, coated tablets, capsules, powders, granules, syrups, solutions or drops, for rectal administration are suppositories, for parenteral administration are solutions, preferably oily or aqueous solutions, also suspensions, emulsions or implants, for topical administration are ointments, creams or dusting powders. The novel compounds can also be lyophilized and the resulting lyophilisates be used, for example, to produce products for injection. The stated compositions can also be sterilized and/or contain ancillary substances such as lubricants, preservatives, stabilizers and/or wetting agents, emulsifiers, salts to influence the osmotic pressure, buffer substances, colorants, flavourings and/or several other active substances, for example one or more vitamins.

The compounds of the formula I according to the invention are, as a rule, administered in analogy to other known products obtainable commercially for the claimed indications (for example imipramine, fluoxetine, clomipramine), preferably in dosages between 0.1 mg and 500 mg, in particular between 5 and 300 mg, per dosage unit. The daily dose is preferably between about 0.01 and 250 mg/kg, in particular between 0.02 and 100 mg/kg, of body weight.

The specific dose for each patient depends, however, on a wide variety of factors, for example on the activity of the specific compound employed, on the age, body weight, general state of health, sex, on the diet, on the time and route of administration, on the rate of excretion, combination of medicinal substances and severity of the particular disorders for which the therapy applies. Oral administration is preferred.

All temperatures are stated in °C. hereinbefore and hereinafter. In the following examples, "usual workup" means: if necessary, water is added, the pH is adjusted if necessary, depending on the constitution of the final product, to values between 2 and 10, extraction is carried out with ethyl acetate or dichloromethane, and the organic phase is separated off, dried over sodium sulfate, evaporated and purified by chromatography on silica gel, there also being separation of the isomers described below, and/or by crystallization. Rf values on silica gel; mobile phase: ethyl acetate/methanol 9:1.

Mass spectrometry:
EI (electron impact ionization): M+
FAB (fast atom bombardment): (M+H)+

EXAMPLE 1

A solution of 5-(methanesulfonyloxymethyl)-3-p-methoxyphenyloxazolidin-2-one [obtainable by reacting 2,3-epoxypropanol with N-benzyl-p-methoxyaniline to give 1-(N-benzyl-p-methoxyanilinopropane-2,3-diol, hydrogenolysis to give 1-p-methoxyanilinopropane-2,3-diol, reacting with diethyl carbonate to give 5-hydroxymethyl-3-p-methoxyphenyloxazolidin-2-one and reaction with $CH_3SO_2Cl$] in acetonitrile is mixed with equimolar amounts of 4-(3-indolyl)piperidine ("A"), potassium iodide and potassium carbonate, heated under reflux for 16 hours and then subjected to the usual workup. This results in 3-(4-methoxyphenyl)-5-[4-(3-indolyl)-1-piperidinylmethyl] oxazolidin-2-one, m.p. 151–153°.

Analogous reaction of "A"
with (5S)-5-(methanesulfonyloxymethyl)-3-p-methoxy-phenyloxazolidin-2-one results in
(5S)-(−)3-(4-methoxyphenyl)-5-[4-(3-indolyl)-1-piperidinylmethyl]oxazolidin-2-one, hydrochloride, m.p. 234–236°, $\alpha_D^{20}$−56° (c=1, methanol);
with (5S)-5-(methanesulfonyloxymethyl)-3-p-chloro-phenyloxazolidin-2-one results in
(5S)-(−)3-(4-chlorophenyl)-5-[4-(3-indolyl)-1-piperidinylmethyl]oxazolidin-2-one, m.p. 188–189°, $\alpha_D^{20}$−28° (c=1, DMSO); hydrochloride, m.p. 260–263°;
with 5-(methanesulfonyloxymethyl)-3-p-cyanophenyl-oxazolidin-2-one results in
3-(4-cyanophenyl)-5-[4-(3-indolyl)-1-piperidinyl-methyl]oxazolidin-2-one.
with 5-(methanesulfonyloxymethyl)-3-phenyloxazolidin-2-one results in
3-phenyl-5-[4-(3-indolyl)-1-piperidinylmethyl]-oxazlidin-2-one;
with 5-(methanesulfonyloxymethyl)-3-p-fluorophenyl-oxazolidin-2-one results in
3-(4-fluorophenyl-5-[4-(3-indolyl)-1-piperidinylmethyl]oxazolidin-2-one.

Analogous reaction of 4-(5H-1,3-dioxolo[4,5-f]-indol-7-yl)piperidine ("B")
with (5S)-5-(methanesulfonyloxymethyl)-3-p-methoxy-phenyloxazolidin-2-one results in
(5S)-(−)3-(4-methoxyphenyl)-5-[4-(5H-1,3-dioxolo [4,5-f]indol-7-yl)-1-piperidinylmethyl]-oxazolidin-2-one, hydrochloride, m.p. 232–234°, $\alpha_D^{20}$−50.5° (c=1, methanol);
with (5S)-5-(methanesulfonyloxymethyl)-3-p-chlorophenyloxazolidin-2-one results in
(5S)-(−)3-(4-chlorophenyl)-5-[4-(5H-1,3-dioxolo [4,5-f] indol-7-yl)-1-piperidinylmethyl]-oxazolidin-2-one.

Analogous reaction of 4-(5-fluoro-3-indolyl)-piperidine ("C")
with (5S)-5-(methanesulfonyloxymethyl)-3-p-methoxy-phenyloxazolidin-2-one results in
(5S)-(−)3-(4-methoxyphenyl)-5-[4-(5-fluoro-3-indolyl)-1-piperidinylmethyl]oxazolidin-2-one, hydrochloride, m.p. 233–234°, $\alpha_D^{20}$−58.5° (c=1, DMSO);

with 5-(methanesulfonyloxymethyl)-3-p-cyanophenyl-oxazolidin-2-one results in
3-(4-cyanophenyl)-5-[4-(5-fluoro-3-indolyl)-1-piperidinylmethyl]oxazolidin-2-one, hydrochloride, m.p. 290–292°;
with (5S)-5-(methanesulfonyloxymethyl)-3-p-cyanophenyl-oxazolidin-2-one results in
(5S)-(−)3-(4-cyanophenyl)-5-[4-(5-fluoro-3-indolyl)-1-piperidinylmethyl]oxazolidin-2-one, hydrochloride, m.p. 203–204°; $\alpha_D^{20}$−36.5° (c=1, DMSO);
with (5R)-5-(methanesulfonyloxymethyl)-3-p-cyanophenyl-oxazolidin-2-one results in
(5R)-(+)3-(4-cyanophenyl)-5-[4-(5-fluoro-3-indolyl)-1-piperidinylmethyl]oxazolidin-2-one, hydrochloride, m.p. 286–287°; $\alpha_D^{20}$+41.5° (c=1, DMSO).

Analogous reaction of 4-(5-cyano-3-indolyl)-piperidine ("D")
with 5-(methanesulfonyloxymethyl)-3-p-cyanophenyl-oxazolidin-2-one results in
3-(4-cyanophenyl)-5-[4-(5-cyano-3-indolyl)-1-piperidinylmethyl]oxazolidin-2-one, hydrochloride, m.p. 290°;
with (5S)-5-(methanesulfonyloxymethyl)-3-p-fluoro-phenyloxazolidin-2-one results in
(5S)-(−)-3-(4-fluorophenyl)-5-[4-(5-cyano-3-indolyl)-1-piperidinylmethyl]oxazolidin-2-one, hydrochloride, m.p. 252–253°;
with (5S)-5-(methanesulfonyloxymethyl)-3-p-cyano-phenyloxazolidin-2-one results in
(5S)-(−)-3-(4-cyanophenyl)-5-[4-(5-cyano-3indolyl)-1-piperidinylmethyl]oxazolidin-2-one, hydrochloride, m.p. 270–271°, $\alpha_D^{20}$−38.7° (c=1, DMSO);
with (5R)-5-(methanesulfonyloxymethyl)-3-p-cyano-phenyloxazolidin-2-one results in
(5R)-(+)-3-(4-cyanophenyl)-5-[4-(5-cyano-3-indolyl)-1-piperidinylmethyl]oxazolidin-2-one, hydrochloride, m.p. 270–272°, $\alpha_D^{20}$+37.7° (c=1, DMSO);
with 5-(methanesulfonyloxymethyl)-3-p-fluorophenyl-oxazolidin-2-one results in
3-(4-fluorophenyl)-5-[4-(5-cyano-3-indolyl)-1-piperidinylmethyl]oxazolidin-2-one, hydrochloride, m.p. 264–268°;
with 5-(methanesulfonyloxymethyl)-3-phenyloxazolidin-2-one results in
3-phenyl-5-[4-(5-cyano-3-indolyl)-1-piperidinylmethyl]-oxazolidin-2-one, hydrochloride hydrate, m.p. 183–185°;
with (5R)-5-(methanesulfonyloxymethyl)-3-p-fluoro-phenyloxazolidin-2-one results in
(5R)-(+)-3-(4-fluorophenyl)-5-[4-(5-cyano-3-indolyl)-1-piperidinylmethyl]oxazolidin-2-one, hydrochloride, m.p. 184–188°, $\alpha_D^{20}$+27.2° (c=1, DMSO).

Analogous reaction of 4-(6-fluoro-3-indolyl)-piperidine ("E")
with (5S)-5-(methanesulfonyloxymethyl)-3-p-cyanophenyl-oxazolidin-2-one results in
(5S)-(−)-3-(4-cyanophenyl)-5-[4-(6-fluoro-3-indolyl)-1-piperidinylmethyl]oxazolidin-2-one, hydrochloride, m.p. 287–288°, $\alpha_D^{20}$−38.4° (c=1, DMSO);
with 5-(methanesulfonyloxymethyl)-3-p-fluorophenyl-oxazolidin-2-one results in
3-(4-fluorophenyl)-5-[4-(6-fluoro-3-indolyl)-1-piperidinylmethyl]oxazolidin-2-one, hydrochloride, m.p. 257–259°;
with (5R)-5-(methanesulfonyloxymethyl)-3-p-cyanophenyl-oxazolidin-2-one results in (5R)-(+)-3-(4-cyanophenyl)-5-[4-(6-fluoro-3-indolyl)-1-piperidinylmethyl]oxazolidin-2-one, hydrochloride, m.p. 288–290°, $\alpha_D^{20}$+38.8° (c=1, DMSO);

with 5-(methanesulfonyloxymethyl)-3-phenyloxazolidin-2-one results in 3-phenyl-5-[4-(6-fluoro-3-indolyl)-1-piperidinyl-methyl]oxazolidin-2-one, hydrochloride, m.p. 234–236°.

EXAMPLE 2

A solution of 1-[4-(3-indolyl)-1-piperidinyl]-3-(4-methoxyanilino)-2-propanol in dichloromethane is mixed with equimolar amounts of ditrichloromethyl carbonate and stirred for 5 hours. The usual workup results in 3-(4-methoxyphenyl)-5-[4-(3-indolyl)-1-piperidinylmethyl]oxazolidin-2-one, m.p. 151–153°.

EXAMPLE 3

Hydrogen is passed for 1 hour through a solution of 5-[4-(3-indolyl)-3,6-dihydro-2H-pyridin-1-ylmethyl]-3-(4-methoxyphenyl)oxazolidin-2-one [obtainable by dehydration of 3-(4-methoxyphenyl)-5-[4-(3-indolyl)-4-hydroxy-1-piperidinylmethyl]oxazolidin-2-one which was prepared by reacting 3-(4-methoxyphenyl)-5-[4-oxo-1-piperidinylmethyl]oxazolidin-2-one with indole] in methanol in the presence of palladium (10% on active carbon). Removal of the catalyst and the usual workup results in 3-(4-methoxyphenyl)-5-[4-(3-indolyl)-1piperidinylmethyl]oxazolidin-2-one, m.p. 151–153°.

The following examples relate to pharmaceutical compositions:

Example A

Vials

A solution of 100 g of an active substance of the formula I and 5 g of disodium hydrogen phosphate in 3 l of double-distilled water is adjusted to pH 6.5 with 2 N hydrochloric acid, sterilized by filtration, dispensed into vials, lyophilized under sterile conditions and sealed sterile. Each vial contains 5 mg of active substance.

Example B

Suppositories

A mixture of 20 g of an active substance of the formula I with 100 g of soya lecithin and 1400 g of cocoa butter is melted, poured into moulds and left to cool. Each suppository contains 20 mg of active substance.

Example C

Solution

A solution is prepared from 1 g of an active substance of the formula I, 9.38 g of NaH$_2$PO$_4$2H$_2$O, 28.48 g of Na$_2$HPO$_4$12H$_2$O and 0.1 g of benzalkonium chloride in 940 ml of double-distilled water. The pH is adjusted to 6.8, and the solution is made up to 1 l and sterilized by irradiation.

Example D

Ointment 500 mg of an active substance of the formula I are mixed with 99.5 g of petrolatum under aseptic conditions.

Example E

Tablets

A mixture of 1 kg of active substance of the formula I, 4 kg of lactose, 1.2 kg of potato starch, 0.2 kg of talc and 0.1 kg of magnesium stearate is compressed to tablets in a conventional way so that each tablet contains 10 mg of active substance.

Example F

Coated Tablets

Tablets are made in analogy to Example E and are then provided in a conventional way with a coating of sucrose, potato starch, talc, tragacanth and dye.

Example G

Capsules 2 kg of active substance of the formula I are packed in a conventional way into hard gelatine capsules so that each capsule contains 20 mg of the active substance.

Example H

Ampoules

A solution of 1 kg of active substance of the formula I in 60 of double-distilled water is sterilized by filtration, dispensed into ampoules, lyophilized under sterile conditions and sealed sterile. Each ampoule contains 10 mg of active substance.

What is claimed is:

1. A compound of the formula I

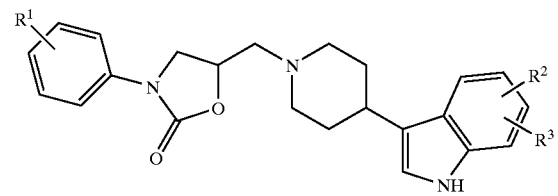

in which

R$^1$ is H, CN, Hal or OA,

R$^2$, R$^3$ are each, independently of one another, H, CN, Hal or OA, or

R$^2$ and R$^3$ together are methylenedioxy,

A is H, CF$_3$ or alkyl, optionally substituted, with 1–6 C atoms and

Hal is F, Cl, Br, I, or a salt thereof.

2. An enantiomer of the compound of the formula I according to claim 1.

3. A compound of the formula I according to claim 1 which is a) (5S)-(−)-3-(4-chlorophenyl)-5-[4-(3-indolyl)-1-piperidinylmethyl]oxazolidin-2-one;

b) 3-(4-cyanophenyl)-5-[4-(5-cyano-3-indolyl)-1-piperidinylmethyl]oxazolidin-2-one;

c) (5S)-(−)-3-(4-cyanophenyl)-5-[4-(6-fluoro-3-indolyl)-1-piperidinylmethyl]oxazolidin-2-one;

d) (5R)-(+)-3-(4-cyanophenyl)-5-[4-(5-fluoro-3-indolyl)-1-piperidinylmethyl]oxazolidin-2-one;

e) (5R)-(+)-3-(4-cyanophenyl)-5-[4-(6-fluoro-3-indolyl)-1-piperidinylmethyl]oxazolidin-2-one;

f) 3-phenyl-5-[4-(5-cyano-3-indolyl)-1-piperidinylmethyl]oxazolidin-2-one;

g) 3-phenyl-5-[4-(6-fluoro-3-indolyl)-1-piperidinylmethyl]oxazolidin-2-one;

or a salt thereof.

4. A process for the preparation of a compound of formula I according to claim 1, which comprises:

a) reacting a compound of the formula II

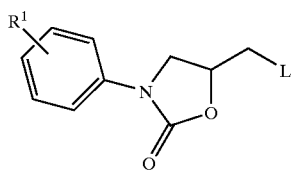

in which $R^1$ has the meaning stated in claim 1, and L is Cl, Br, I or a free or reactively functionally modified OH group,
with a compound of the formula III

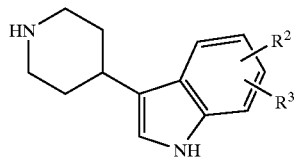

in which $R^2$ and $R^3$ have the meanings given in claim 1, and optionally converting a basic compound of the formula I by treatment with an acid into a salt thereof.

5. A process for the production of a pharmaceutical composition, comprising combining together a compound of the formula I according to claim 1 and/or one of its physiologically tolerated salts or one of its enantiomers with at least one solid, liquid or semiliquid excipient or ancillary substance and, where appropriate, in combination with one or more other active substances, into a suitable dosage form.

6. A pharmaceutical composition comprising at least one compound of claim 1 or at least one of its physiologically acceptable salts, and a pharmaceutically acceptable carrier.

7. A method comprising administering a compound to an animal of the formula I according to claim 1 or a physiologically acceptable salt thereof for controlling a sequela of stroke or a cerebral ischaemia, or for treating an obsessive-compulsive disorder (OCD), an anxiety state, a panic attack, depression, psychosis, schizophrenia or Parkinson's disease.

8. A compound of the formula I according to claim 1 or a physiologically acceptable salt thereof which exhibits a $5\text{-HT}_{2A}$ antagonist with 5-HT reuptake-inhibiting effect wherein Hal is F or Cl.

9. A method of producing a pharmaceutical composition comprising combining a compound according to claim 1 or a physiologically acceptable salt thereof with a pharmaceutically acceptable carrier.

10. A pharmaceutical preparation comprising a compound according to claim 1 and a physiologically acceptable carrier.

11. A compound of the formula I

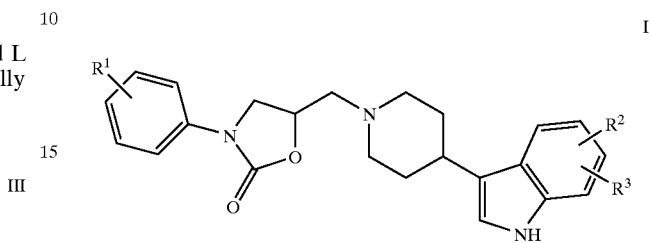

wherein $R^1$ is H, CN, Hal or OA;

$R^2$, $R^3$ are each, independently of one another, H, CN, Hal, or OA; or $R^2$ and $R^3$ together are methylenedioxy;

A is methy, ethyl, propyl, isopropyl, butyl, isobutyl, sec-butyl, pentyl, 1-, 2- or 3-methylbutyl, 1,1-, 1,2- or 2,2-dimethylpropyl, 1-ethylpropyl, hexyl, 1-, 2-, 3-, or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, fluoromethyl, difluoromethyl, trifluoromethyl, 1,1,1-trichloroethyl or pentafluoroethyl; and Hal is F, Cl, Br, or I;

or a salt thereof.

12. A compound of formula I according to claim 1 wherein at least one of $R^1$, $R^2$ or $R^3$ is OA which is hydroxyl or alkoxy.

13. A process according to claim 5 wherein the ancillary substance is a lubricant, a preservative, a stabilizer, a wetting agent, emulsifier, salt to influence the osmotic pressure, buffer substance, colorant, flavouring and/or vitamin.

* * * * *

UNITED STATES PATENT AND TRADEMARK OFFICE
CERTIFICATE OF CORRECTION

PATENT NO.    : 6,462,056 B1                                      Page 1 of 1
DATED         : October 8, 2002
INVENTOR(S)   : Böttcher et al.

It is certified that error appears in the above-identified patent and that said Letters Patent is hereby corrected as shown below:

<u>Title page,</u>
Item [54], change "OXAZOLIDINES AS 5HT$_{2A}$-ANTAGONISTS" to
-- OXAZOLIDINES --.

<u>Column 12,</u>
Line 28, after "sec-butyl," insert -- tert-butyl --.

Signed and Sealed this

Fifteenth Day of July, 2003

JAMES E. ROGAN
*Director of the United States Patent and Trademark Office*